US012788703B2

(12) United States Patent
Macneill et al.

(10) Patent No.: US 12,788,703 B2
(45) Date of Patent: Nov. 10, 2026

(54) NAIL COATINGS BASED ON PHOTOCURABLE COMPOSITIONS

(71) Applicant: Arkema France, Colombes (FR)

(72) Inventors: Christopher Macneill, Exton, PA (US); Ling Li, Exton, PA (US)

(73) Assignee: Arkema France, Puteaux (FR)

( * ) Notice: Subject to any disclaimer, the term of this patent is extended or adjusted under 35 U.S.C. 154(b) by 633 days.

(21) Appl. No.: 17/630,959

(22) PCT Filed: Jul. 27, 2020

(86) PCT No.: PCT/IB2020/000654
§ 371 (c)(1),
(2) Date: Jan. 28, 2022

(87) PCT Pub. No.: WO2021/019306
PCT Pub. Date: Feb. 4, 2021

(65) Prior Publication Data

US 2022/0273547 A1 Sep. 1, 2022

Related U.S. Application Data

(60) Provisional application No. 62/880,684, filed on Jul. 31, 2019.

(51) Int. Cl.
*A61K 8/81* (2006.01)
*A45D 34/04* (2006.01)
*A61Q 3/02* (2006.01)
*C08F 2/50* (2006.01)

(52) U.S. Cl.
CPC .............. *A61K 8/8152* (2013.01); *A61Q 3/02* (2013.01); *C08F 2/50* (2013.01); *A45D 34/045* (2013.01)

(58) Field of Classification Search
CPC ........... A61K 8/8152; A61Q 3/02; C08F 2/50; A45D 34/045
See application file for complete search history.

(56) References Cited

U.S. PATENT DOCUMENTS

| | | | |
|---|---|---|---|
| 3,287,433 | A | 11/1966 | Burk, Jr. et al. |
| 3,657,391 | A | 4/1972 | Curfman |
| 3,808,180 | A | 4/1974 | Owens |
| 3,985,704 | A | 10/1976 | Jones et al. |
| 4,096,202 | A | 6/1978 | Farnham et al. |
| 4,180,494 | A | 12/1979 | Fromuth et al. |
| 4,260,693 | A | 4/1981 | Liu |
| 4,299,928 | A | 11/1981 | Witman |
| 5,632,973 | A | 5/1997 | Keller |
| 5,773,520 | A | 6/1998 | Bertelo et al. |
| 6,244,274 | B1 | 6/2001 | Sirdesai et al. |
| 8,367,742 | B2 | 2/2013 | Vu et al. |
| 8,901,199 | B2 | 12/2014 | Vu et al. |
| 9,084,738 | B2 | 7/2015 | Haile |
| 2004/0077766 | A1 | 4/2004 | De Cooman et al. |
| 2018/0001116 | A1 | 1/2018 | Sirdesai et al. |
| 2018/0092827 | A1 | 4/2018 | Sheran et al. |
| 2018/0325788 | A1 | 11/2018 | Takemoto |
| 2018/0325789 | A1 | 11/2018 | Takemoto |

FOREIGN PATENT DOCUMENTS

| | | | |
|---|---|---|---|
| JP | 2014201688 | A2 | 10/2014 |
| WO | WO2017217983 | A1 | 12/2017 |
| WO | WO2017220791 | A1 | 12/2017 |

*Primary Examiner* — Robert A Wax
*Assistant Examiner* — Olga V. Tcherkasskaya
(74) *Attorney, Agent, or Firm* — Christopher R. Lewis

(57) ABSTRACT

Photocurable compositions which include a). at least one (meth)acrylate-functionalized monomer; b). at least one (meth)acrylate-functionalized oligomer; c). particles of at least one core/shell copolymer; and d). at least one photoinitiator are useful for forming durable, impact resistant coatings on nails.

22 Claims, No Drawings

NAIL COATINGS BASED ON PHOTOCURABLE COMPOSITIONS

CROSS-REFERENCE TO RELATED APPLICATIONS

This application is a U.S. national stage application under 35 U.S.C. § 371 of international application number PCT/IB2020/000654, filed Jul. 27, 2020, which claims priority to U.S. patent application No. 62/880,684, filed Jul. 31, 2019.

FIELD OF THE INVENTION

The present invention relates to nail coatings obtained from certain photocurable compositions containing impact modifying core/shell copolymers and having enhanced mechanical properties and durability, methods of forming nail coatings from such photocurable compositions, articles which include a container with such a photocurable composition contained therein, and kits containing a packaged photocurable composition and instructions for preparing nail coatings therefrom.

BACKGROUND OF THE INVENTION

Acrylic nail formulations are well-known and can help enhance the appearance of nails (e.g., human fingernails and toenails) by allowing a user to shape the formulation into various configurations. Traditional acrylic nail formulations are made up of two parts: 1) a photo-crosslinkable liquid monomer and 2) an acrylic polymer powder containing activator/initiator. The two components are mixed together and applied to the nail to be shaped and sculpted by a manicurist using various tools. Acrylic nails made from such traditional formulations can be brittle and suffer from low impact strength. Impact resistance is important in the context of nail embellishments because consumers expect acrylic nails to be durable and to be capable of withstanding external forces for extended periods of time without cracking, breaking, chipping or otherwise being degraded in appearance.

In recent years, a new type of nail formulation has been developed which is a one part system containing photocurable oligomer(s), photocurable monomer(s), pigment(s) and possibly one or more other additives. Such formulations will typically have a viscosity similar to that of traditional nail polish and may be applied to a nail surface in much the same way as a traditional nail polish, then cured in place using ultraviolet (UV) radiation to give a protective/decorative coating that generally is capable of lasting up to fourteen days. Such formulations can be referred to as "UV gel polishes" and are described for example in U.S. Pat. Nos. 8,901,199B2; 8,367,742B2; and 9084738B2. A hybrid variation on based on UV gel polish and traditional acrylic nail formulations has been disclosed in which the UV gel polish formulation is supplemented by a polymeric powder, such as a powder based on polymethyl methacrylate (PMMA). Such powders have a particle size of at least 1 micron (i.e., at least 1000 nm). See, for example, U.S. Pat. No. 6,244,274B2; US Pat. Pub. No. 2018/0092827A1; and WO 2017/217983A1.

Despite such advances in nail coating technology, there is still a need for improved formulations that, when cured, provide nail coatings with enhanced durability and resistance to external forces such as impact forces.

SUMMARY OF THE INVENTION

The present invention utilizes photocurable compositions containing at least the following components:

a). at least one (meth)acrylate-functionalized monomer;
b). at least one (meth)acrylate-functionalized oligomer;
c). particles of at least one core/shell copolymer; and
d). at least one photoinitiator.

Such compositions may be clear or pigmented and are formulated to be usable as one part systems, that is, formulations capable of being applied to a nail surface and then cured by exposure to actinic radiation (e.g., UV or visible light) without having to first be admixed with a second component. By including the core/shell copolymer particles in the photocurable composition, the mechanical properties and durability of the resulting nail coating may be significantly improved as compared to a cured nail coating prepared using an analogous formulation that does not contain such core/shell copolymer particles. In addition, due to their small size, these impact modifying core/shell copolymer particles can have little to no effect on the optical transparency of the cured product, which is not the case with PMMA-based particles that are greater than 1 micron in size.

The photocurable compositions may be formulated to have the following further attributes or properties:

1). A relatively high viscosity and liquid consistency which permit the composition to be readily applied to a nail surface and shaped into a desired configuration of significant thickness prior to being photocured, without running or dripping;
2). No need to mix with other components prior to application and curing;
3). A high degree of homogeneity and physical stability (e.g., little or no tendency of the components of the composition to separate, even upon prolonged storage);
4). Long open time (permitting an extended period during which the nail may be sculpted);
5). Low odor;
6). Low shrinkage upon curing;
7). High transparency when cured; and/or
8). Low content of volatiles (i.e., little or no non-reactive solvent).

The present invention provides a coating on a nail, wherein the coating is the photocured product of such a photocurable composition.

Also provided by the present invention is a method of forming a coating on a nail, comprising the steps of:

a) placing a photocurable composition as described herein onto a surface of a nail; and
b) exposing the photocurable composition to actinic radiation, in particular ultraviolet or visible light.

A packaged article is also provided by the present invention, wherein the packaged article comprises a container and a photocurable composition as described herein disposed within the container, wherein the packaged article has a dispensing component capable of dispensing the photocurable composition from the container.

The present invention additionally provides a kit, comprising a packaged article comprising a container and a photocurable composition as described herein disposed within the container, at least one application device, and instructions for dispensing, applying and curing the photocurable composition to provide a nail coating.

DETAILED DESCRIPTION OF CERTAIN EMBODIMENTS OF THE INVENTION

The present invention employs a photocurable composition which comprises, consists essentially of, or consists of:

a). at least one (meth)acrylate-functionalized monomer;
b). at least one (meth)acrylate-functionalized oligomer;

c). particles of at least one core/shell copolymer; and d). at least one photoinitiator.

One or more additional components may additionally be present, in particular pigments and/or colorants and possibly (meth)acrylic polymers as described in more detail henceforth. The photocurable composition is used to form a cosmetic coating for nails and may be a liquid having a relatively high viscosity at room temperature that permits the photocurable composition to be applied to the surface of a nail (i.e., a nail plate) and then readily shaped (sculpted) by a nail technician or other operator to a desired configuration on the nail surface, followed by exposure to ultraviolet (UV) light or other actinic radiation to photopolymerize the shaped photocurable composition to form a hard, durable, impact-resistant nail coating. The photocurable composition alternatively may be a liquid having a relatively low viscosity at room temperature that permits the photocurable composition to be readily applied as a thin layer to the surface of a nail (i.e., a nail plate), followed by exposure to ultraviolet (UV) light or other actinic radiation to photopolymerize the thin layer of photocurable composition to form a hard, durable, impact-resistant nail coating. In particular, the presence of the core/shell copolymer particles help to significantly improve the impact properties of the cured coating (i.e., resistance to chipping, breaking, scuffing) while maintaining good optical transparency and high gloss over time.

Core/Shell Copolymer

Core/shell copolymers useful in the context of the present invention may be generally described as polymeric substances, typically in particulate (particle form), comprised of a core (inner portion) comprised of a first polymer ("core polymer") and at least one shell (outer portion) substantially or completely surrounding the core comprised of a second polymer ("shell polymer"). Typically, the shell polymer has a glass transition temperature which is higher than the glass transition temperature of the core polymer. The glass transition temperatures of the polymers of the core/shell copolymers may be measured according to standard ISO 11357-2:199. Generally speaking, the glass transition temperature of the core polymer is preferentially less than 20° C., less than 10° C. or less than 0° C., for example between −140° C. and 0° C. Preferentially, the glass transition temperature of the shell polymer is greater than 20° C. or greater than 30° C., for example between 30° C. and 250° C. The difference between the glass transition temperatures of the core polymer and the shell polymer may be at least 10° C., at least 20° C., or at least 30° C., according to various embodiments of the invention. Thus, the core polymer may be considered a "soft" polymer (and may be elastomeric or rubbery in nature), whereas the shell polymer may be regarded as a "hard" (non-elastomeric) polymer.

The shell part of the core/shell copolymer may preferentially comprise, in polymerized form: an alkyl methacrylate in which the alkyl chain comprises from 1 to 12 carbon atoms (i.e., C1-C12 alkyl methacrylates) and preferably from 1 to 4 carbon atoms, such as methyl methacrylate; and/or a vinyl aromatic organic compound comprising from 6 to 12 carbon atoms, such as styrene; and/or acrylonitrile. The shell part of the core/shell copolymer may or may not be crosslinked.

The core portion of the core/shell copolymer advantageously comprises, in polymerized form: a conjugated diene comprising from 4 to 12 and preferably from 4 to 8 carbon atoms (such as butadiene); or an alkyl acrylate in which the alkyl chain comprises from 1 to 12 and preferably from 1 to 8 carbon atoms (such as butyl acrylate). The alkyl chain may be a linear alkyl chain or a branched alkyl chain.

The core/shell copolymer may, for example, be selected from: a core/shell copolymer with a core comprising butadiene (in polymerized form) and a shell comprising methyl methacrylate, ethyl acrylate, butyl acrylate, methacrylic acid and/or styrene (in polymerized form); a core/shell copolymer with a core comprising butyl acrylate, n-octyl acrylate and/or 2-ethylhexyl acrylate (in polymerized form) and a shell comprising methyl methacrylate (in polymerized form); or a core/shell copolymer with a core comprising butadiene (in polymerized form) and a shell comprising a mixture of acrylonitrile and styrene (in polymerized form). In the aforementioned embodiments, the butadiene comprising the core may be copolymerized with styrene.

The following types of core/shell copolymers are examples of core/shell copolymers particularly suitable for use in the present invention:

a). Core/shell copolymers comprising, consisting essentially of or consisting of a core comprised of, consisting essentially of or consisting of butyl acrylate in polymerized form (e.g., a homopolymer of butyl acrylate or a copolymer of butyl acrylate and at least one co-monomer, wherein the copolymer contains at least 80%, at least 85%, at least 90%, at least 95%, or at least 99% by weight of butyl acrylate in polymerized form) and a shell comprised of, consisting essentially of or consisting of methyl methacrylate in polymerized form (e.g., a homopolymer of methyl methacrylate or a copolymer of methyl methacrylate and at least one co-monomer, wherein the copolymer contains at least 80%, at least 85%, at least 90%, at least 95%, or at least 99% by weight of methyl methacrylate in polymerized form); and b). Core/shell copolymers comprising, consisting essentially of or consisting of a core comprised of, consisting essentially of or consisting of styrene and butadiene in copolymerized form (e.g., a copolymer of butadiene and styrene, optionally copolymerized with at least one additional co-monomer in an amount of up to 10% by weight based on the copolymer weight) and a shell comprised of, consisting essentially of or consisting of methyl methacrylate in polymerized form (e.g., a homopolymer of methyl methacrylate or a copolymer of methyl methacrylate and at least one co-monomer, wherein the copolymer contains at least 80%, at least 85%, at least 90%, at least 95%, or at least 99% by weight of methyl methacrylate in polymerized form).

The mass amount of core is advantageously within the range of from 10% to 99%, for example from 60% to 95%, of the total mass of the core/shell copolymer. The particle size of the core/shell copolymer is less than 1000 nm, advantageously between 10 and 900 nm, between 25 and 700 nm, or between 40 and 600 nm.

Examples of core polymers that may be mentioned include rubbers; polysiloxanes; homopolymers and copolymers of butadiene, butyl acrylate, methyl methacrylate, ethyl acrylate, 2-ethylhexyl acrylate, and/or butyl acrylate; isoprene homopolymers; isoprene-butadiene copolymers; copolymers of isoprene with not more than 98% by weight of a vinyl monomer; and copolymers of butadiene with not more than 98% by weight of a vinyl monomer. The vinyl monomer may be styrene, an alkylstyrene, acrylonitrile, an alkyl (meth)acrylate, an alkyl acrylate, butadiene or isoprene. The core polymer may also comprise siloxane, optionally copolymerized with an alkyl acrylate. The core of the core/shell copolymer may be totally or partially crosslinked. To achieve crosslinking, at least difunctional monomers may be added during the preparation of the core, and these monomers may be chosen from poly(meth)acrylic esters of polyols such as butylene di(meth)acrylate and trimethylolpropane trimethacrylate. Other multifunctional monomers are, for example, divinylbenzene, trivinylbenzene, vinyl acrylate and vinyl methacrylate, and triallyl cyanurate. The core may also be crosslinked by introducing therein, by grafting or as comonomer during the polymerization, unsaturated functional monomers such as unsaturated carboxylic acid anhydrides, unsaturated carboxylic acids and unsaturated epoxides. Examples that may be mentioned include maleic anhydride, (meth)acrylic acid and glycidyl methacrylate. Crosslinking may also be performed using the intrinsic reactivity of monomers, for example dienes.

The core/shell copolymer may contain a single shell or a plurality of shells (i.e., two or more shells, wherein the shells may differ with respect to their monomer composition, molecular weight, degree of crosslinking or other characteristics. The shell(s) of the core/shell copolymer may be, for example, homopolymers or copolymers of styrene, of an alkylstyrene, of a C1-C4 alkyl (meth)acrylate, of methyl methacrylate, of butyl acrylate, of ethyl acrylate, or copolymers comprising at least 70% by weight of one of the preceding monomers and at least one comonomer chosen from the other preceding monomers, another alkyl (meth) acrylate, vinyl acetate and acrylonitrile. The shell may be functionalized by introducing therein, by grafting or as comonomer during the polymerization, unsaturated functional monomers such as unsaturated carboxylic acid anhydrides, unsaturated carboxylic acids and unsaturated epoxides. Examples that may be mentioned include maleic anhydride, (meth)acrylic acid, glycidyl methacrylate, hydroxyethyl methacrylate and alkyl(meth)acrylamides. Examples that may be mentioned include core/shell copolymers with a shell made of polystyrene and core/shell copolymers with a shell made of PMMA. The shell may also contain imide functions, either by copolymerization with a maleimide, or by chemical modification of the PMMA with a primary amine. Advantageously, the molar percentage of imide functions is from 30% to 60% (relative to the shell as a whole). Core/shell copolymers containing two shells may also be used, wherein one shell is made of polystyrene and the other shell on the exterior is made of PMMA. Examples of core/shell copolymers and processes for preparing them are described in the following patents, each of which is incorporated herein by reference in its entirety for all purposes: U.S. Pat. Nos. 4,180,494, 3,808,180, 4,096,202, 4,260,693, 3,287,443, 3,657,391, 4,299,928, 3,985,704, 5,773,520.

According to certain embodiments, the core may represent 5% to 95%, 50% to 95%, or 60% to 90% by mass of the core/shell copolymer, and the shell(s) may represent 95% to 5%, 50% to 5%, or 40% to 10% by mass of the core/shell copolymer.

The polymers referred to in the art as "multistage polymers" are also useful as the core/shell copolymer component of the photocurable compositions of the present invention. Multistage polymers are described, for example, in the following published applications, each of which is incorporated herein by reference in its entirety for all purposes: WO 2016/102666; US 2017/0369696; WO 2017/121749; WO 2017/121750; WO 2017/220791; WO 2018/002259; WO 2018/002260; WO 2018/002273; FR 17 56649; and FR 17 56647.

The amount of core/shell copolymer included in the photocurable composition may be varied as may be desired depending upon the type of core/shell copolymer used, the attributes targeted in the cured nail coating, and the types of polymerizing organic substances used, among possibly other factors. According to various aspects of the invention, the photocurable composition may comprise at least 1%, at least 5%, or at least 10% by weight core/shell copolymer, based on the total weight of the photocurable composition. In other aspects, the photocurable composition may comprise not more than 50%, not more than 45%, or not more than 40% by weight core/shell copolymer, based on the total weight of the photocurable composition. The photocurable composition thus, for example, may be comprised of from 1 to 50%, 5 to 45%, or 10 to 40% by weight of the particles of the at least one core/shell copolymer based on the total weight of the photocurable composition.

In accordance with certain embodiments, the photocurable composition may comprise 1 to 200, 5 to 100, or 15 to 70 parts by weight core/shell copolymer per 100 parts by weight of the total weight of polymerizing organic substances (e.g., the total weight of polymerizing monomer+polymerizing oligomer).

Core/shell copolymers suitable for use in the present invention include the core/shell copolymers sold by Arkema under the brand names Biostrength®, Durastrength®, and Clearstrength® impact modifiers.

An important advantage which is achieved by the use of the above-described core/shell copolymers is that such core/shell copolymers exhibit little or no tendency to impart haziness to a cured nail coating prepared from a photocurable composition in accordance with the present invention. Thus, it is possible to formulate photocurable compositions containing such core/shell copolymer particles which when photocured are capable of providing a highly transparent cured nail coating, even at relatively high loadings of core/shell copolymer.

(Meth)acrylic Polymers

The photocurable composition of the present invention may optionally contain one or more (meth)acrylic polymers. However, such a (meth)acrylic polymer is not required and photocurable compositions which are free of any (meth) acrylic polymer are also contemplated by the present invention. As used herein, the term "(meth)acrylic polymer" means a polymer which does not have a core/shell structure and which comprises one or more (meth)acrylic monomers (in polymerized form) wherein the (meth)acrylic monomer(s) make up 50 wt % or more of the (meth)acrylic polymer. The term "(meth)acrylic monomer," as used herein, means any type of polymerizable monomer containing one or more acrylic and/or methacrylic functional groups.

The presence of (meth)acrylic polymer in the photocurable composition can help to facilitate the dispersion and stabilization of the core/shell copolymer, both in the photocurable composition and a cured article prepared therefrom. In the absence of the (meth)acrylic polymer, the core/shell copolymer, which typically is in the form of particles, may tend to agglomerate and settle out of the photocurable composition (rendering the photocurable composition non-homogeneous). Thus, including the (meth)acrylic polymer may lead to a homogeneous dispersion of the core/shell copolymer in the photocurable composition, which facilitates the formation of a homogeneous cured article prepared by curing the photocurable composition. An ideal homogeneous dispersion of the core/shell copolymer in a matrix has no agglomerates after the core/shell copolymer is combined with the monomer(s) and oligomer(s) (which may be generically referred to as "polymerizing organic substances"). Thus, a liquid photocurable composition comprising a (meth)acrylic polymer, a core/shell copolymer and a polymerizing organic substance may possess or exhibit a better dispersion of the core/shell copolymer than an analogous composition not comprising the (meth)acrylic polymer. Further, a liquid photocurable composition comprising a (meth) acrylic polymer, a core/shell copolymer and a polymerizing organic substance may be less viscous than an analogous composition not comprising the (meth)acrylic polymer.

The molecular weight of the (meth)acrylic polymer is not particularly limited and may be varied as may be needed or desired in order to impart certain characteristics or properties to the photocurable composition and/or cured articles prepared therefrom. The (meth)acrylic polymer may, for example, have a weight average molecular weight of from 2000 g/mol to 1,000,000 g/mol.

In a first embodiment, the (meth)acrylic polymer may have a weight average molecular weight (Mw) of at least 100,000 g/mol, more than 100,000 g/mol, more than 105,000 g/mol, more than 110,000 g/mol, more than 120,000 g/mol, more than 130,000 g/mol, or more than 140,000 g/mol.

The (meth)acrylic polymer may have a weight average molecular weight ($M_w$) below 1,000,000 g/mol, below 900,000 g/mol, below 800,000 g/mol, below 700,000 g/mol, below 600,000 g/mol, below 550,000 g/mol, below 500,000 g/mol, or below 450,000 g/mol.

For example, the weight average molecular weight (Mw) of the (meth)acrylic polymer (PI), according to the first preferred embodiment, is preferably between 100,000 g/mol and 1,000,000 g/mol, preferably between 105,000 g/mol and 900,000 g/mol, more preferably between 110,000 g/mol and 800,000 g/mol, advantageously between 120,000 g/mol and 700,000 g/mol, more advantageously between 130,000 g/mol and 600,000 g/mol, and most advantageously between 140,000 g/mol and 500,000 g/mol.

In a second embodiment, the (meth)acrylic polymer has a weight average molecular weight $M_w$ of less than 100,000 g/mol, less than 90,000 g/mol, more less than 80,000 g/mol, less than 70,000 g/mol, less than 60,000 g/mol, less than 50,000 g/mol, or less than 40,000 g/mol.

In the second embodiment, the (meth)acrylic polymer may have a weight average molecular weight ($M_w$) above 2000 g/mol, above 3000 g/mol, above 4000 g/mol, above 5000 g/mol, above 6000 g/mol, above 6500 g/mol, above 7000 g/mol, above 10,000 g/mol, or above 12,000 g/mol.

The weight average molecular weight ($M_w$) of the (meth) acrylic polymer in the second embodiment may be between 2000 g/mol and 100,000 g/mol, between 3000 g/mol and 90,000 g/mol, between 4000 g/mol and 80,000 g/mol, between 5000 g/mol and 70,000 g/mol, between 6000 g/mol and 50,000 g/mol, or between 10,000 g/mol and 40,000 g/mol.

According to certain embodiments of the invention, the (meth)acrylic polymer may comprise at least 50 wt %, at least 60 wt %, or at least 70 wt % of one or more monomers selected from the group consisting of C1 to C12 alkyl (meth)acrylates. For example, the (meth)acrylic polymer may comprise at least 50 wt %, at least 60 wt %, at least 70 wt % or at least 80% of one or more monomers chosen from C1 to C4 alkyl methacrylate monomers, C1 to C8 alkyl acrylate monomers and mixtures thereof.

In certain embodiments, the glass transition temperature (Tg) of the (meth)acrylic polymer is 30° C. or higher, e.g., between 30° C. and 150° C. The glass transition temperature of the (meth)acrylic polymer (PI) may, for example, be between 40° C. and 150° C., between 45° C. and 150° C., or between 50° C. and 150° C.

According to certain embodiments, the (meth)acrylic polymer is not crosslinked. According to other embodiments, the (meth)acrylic polymer is a thermoplastic polymer. The (meth)acrylic polymer may be a homopolymer or a copolymer, wherein "copolymer" refers to a polymer containing two or more different monomers in polymerized form. The term "thermoplastic polymer" as used herein means a polymer that turns to a liquid or becomes more liquid or less viscous when heated and that can take on new shapes by the application of heat and pressure. The (meth) acrylic polymer, in certain embodiments, is not grafted on any other polymer or polymers, or at least a portion of the (meth)acrylic polymer is not granted on any other polymer or polymers.

In a first embodiment, the (meth)acrylic polymer comprises (in polymerized form) from 50 wt % to 100 wt % methyl methacrylate, from 80 wt % to 100 wt % methyl methacrylate, or from 80 wt % to 99.8 wt % methyl methacrylate and from 0.2 wt % to 20 wt % of a C1 to C8 alkyl acrylate monomer. The C1 to C8 alkyl acrylate monomer may be selected from the group consisting of methyl acrylate, ethyl acrylate and butyl acrylate, according to certain non-limiting embodiments.

In a second embodiment, the (meth)acrylic polymer comprises (in polymerized form) between 0 wt % and 50 wt % of one or more functional monomers. For example, the (meth)acrylic polymer may comprise between 0 wt % and 30 wt %, between 1 wt % and 30 wt %, between 2 wt % and 30 wt %, between 3 wt % and 30 wt %, between 5 wt % and 30 wt %, or between 5 wt % and 30 wt % of the functional monomer(s).

The functional monomer of the second preferred embodiment may be a (meth)acrylic monomer. The functional monomer(s) may have the formula (1) or (2):

(1)

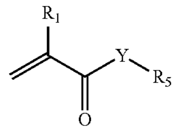

(2)

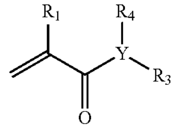

wherein in both formulas (1) and (2), $R_1$ is selected from H or $CH_3$; and in formula (1) Y is O, $R_5$ is H or an aliphatic or aromatic radical having at least one atom that is not C or H; and in formula (2) Y is N and $R_4$ and $R_3$ are independently selected from H or an aliphatic or aromatic radical.

Preferably the functional monomer(s) is or are selected from the group consisting of glycidyl (meth)acrylate; (meth) acrylic acid; (meth)acrylamides such as, for example, dimethylacrylamide; 2-methoxyethyl (meth)acrylate; 2-aminoethyl (meth)acrylates (which may optionally be quaternized; (meth)acrylate monomers comprising a phosphonate or phosphate group; alkyl imidazolidinone (meth)acrylates, and polyethylene glycol (meth)acrylates and combinations thereof. Preferably, the polyethylene glycol group of a polyethylene glycol (meth)acrylate has a number average molecular weight ranging from 400 g/mol to 10,000 g/mol.

According to certain embodiments of the invention, the (meth)acrylic polymer does not contain any functional groups capable of participating in the curing/polymerization which takes place when the photocurable composition is cured. In such embodiments, the (meth)acrylic polymer may be regarded as non-reactive.

In accordance with certain embodiments of the invention, the (meth)acrylic polymer may be soluble at 25° C. in the organic polymerizing substances (the mixture of monomer(s) and oligomer(s) present in the photocurable composition. That is, the organic polymerizing substances function as a solvent for the (meth)acrylic polymer(s). Thus, the combination of (meth)acrylic polymer(s), monomer(s) and oligomer(s) may be a homogeneous (single phase) liquid at 25° C. "Soluble" means that within a certain time the (meth)acrylic polymer(s) when contacted with the polymerizing organic substances dissolve and a solution of the (meth)acrylic polymer(s) in the polymerizing organic substances is obtained. The solubility of the (meth)acrylic polymer(s) in the polymerizing organic substances can be simply tested by mixing the materials at 25° C. under agitation and visually inspecting the mixture.

If present in the photocurable composition, the (meth) acrylic polymer may be included in any suitable amount such as up to 80%, up to 70%, up to 60%, up to 50%, up to 40%, up to 30%, up to 20%, up to 10%, or up to 5% by weight based on the total weight of the photocurable composition.

Polymerizing Organic Substances

The photocurable compositions utilized in the present invention are comprised of polymerizing organic substances. As used herein, the term "polymerizing" means capable of participating in a polymerization or curing reaction to form a polymeric structure. The polymerizing organic substances may be monomeric and/or oligomeric in structure and may be characterized as containing one, two, three or more polymerizing functional groups per molecule. Suitable polymerizing functional groups include in particular functional groups capable of participating in chain-growth and ring-opening polymerization mechanisms, such as ethylenically and ethnically unsaturated functional groups (e.g., (meth)acryloyl, vinyl, olefinic and alkyne functional groups) and heterocyclic-functional groups (e.g., epoxide and oxetane functional groups). Polymerizing functional groups which polymerize via free radical and/or cationic mechanisms are particularly preferred. A polymerizing organic substance may include more than one type of polymerizing functional group. The molecular weight of suitable polymerizing organic substances is not particularly limited and may, for example, be from 120 to 50,000 g/mol or from 150 to 25,000 g/mol (in the case where the polymerizing organic substance is an oligomer, "molecular weight" refers to number average molecular weight as determined by gel permeation chromatography using polystyrene calibration standards). Combinations of different polymerizing organic substances are used in the photocurable compositions of the present invention. In particular, the photocurable compositions comprise at least one polymerizing monomer and at least one polymerizing oligomer.

According to certain embodiments, the total weight of oligomer in the photocurable composition is at least as much as the total weight of monomer. For example, the weight ratio of polymerizing oligomer:polymerizing monomer may be from 50:50 to 90:10.

According to other embodiments, the total weight of monomer in the photocurable composition is at least as much as the total weight of oligomer. For example, the weight ratio of polymerizing monomer:polymerizing oligomer may be from 50:50 to 90:10.

Preferably, the polymerizing organic substances are selected such that in combination as present in the photocurable composition the combination is a liquid at least in the temperature range between 0° C. and 60° C.

Suitable illustrative types of polymerizing organic substances that may be mentioned include, but are not limited to, epoxides (oxiranes), oxetanes, oxolanes, cyclic acetals, and other cyclic ethers, cyclic lactones, vinyl compounds (both aliphatic and aromatic), cyanoacrylates, (meth)acrylamides, and (meth)acrylates (which are particularly preferred). As used herein, the term "(meth)acrylate" refers to both acrylate ($—O—C(=O)—CH=CH_2$) and methacrylate ($—O—C(=O)—C(CH_3)=CH_2$) functional groups.

A polymerizing organic substance contains at least one moiety capable of participating in a polymerization or curing reaction whereby a plurality of polymerizing organic substance molecules become covalently bonded to each other to form a polymeric structure. Suitable reactive moieties include sites of ethylenic unsaturation (i.e., carbon-carbon double bonds, C=C). Such sites of ethylenic unsaturation can be provided, for example, by (meth)acryloyl, maleyl, allyl, propenyl, and/or vinyl groups. As used herein, the term "(meth)acryloyl" is intended to both include methacryloyl and acryloyl, as found in (meth)acrylates and (meth)acrylamides.

As previously mentioned, ethylenically unsaturated functional groups suitable for use in the polymerizing organic substances of the photocurable composition include groups containing at least one carbon-carbon double bond, in particular a carbon-carbon double bond capable of participating in a reaction (e.g., a free radical reaction) wherein at least one carbon of the carbon-carbon double bond becomes covalently bonded to an atom, in particular a carbon atom, in a second molecule. Such reactions may result in a polymerization or curing whereby the organic substance(s) containing one or more ethylenically unsaturated functional groups become(s) part of a polymerized matrix or polymeric chain. The carbon-carbon double bond may, for example, be present as part of an α,β-unsaturated carbonyl moiety, e.g., an α,β-unsaturated ester moiety such as an acrylate functional group ($H_2C=CH—C(=O)O—$) or a methacrylate functional group ($H_2C=C(CH_3)—C(=O)O—$). A carbon-carbon double bond may also be present in the ethylenically unsaturated functional group in the form of a vinyl group $—CH=CH_2$ or an allyl group, $—CH_2—CH=CH_2$.

In certain embodiments, the photocurable compositions employed in the present invention are characterized by comprising at least one (meth)acrylate-functionalized organic substance. A (meth)acrylate-functionalized organic substance may be described as an organic substance bearing one or more (meth)acrylate functional groups per molecule. As used herein, the term "(meth)acrylate" refers to both acrylate and methacrylate functional groups. (Meth)acrylate-functionalized organic substances suitable for use in the present invention may be generally described as ethylenically unsaturated organic substances containing at least one carbon-carbon double bond alpha to an ester group (a compound containing at least one α,βunsaturated ester moiety), in particular a carbon-carbon double bond capable of participating in a free radical reaction, in particular a reaction initiated by ultraviolet radiation or electron beam radiation. Such reactions may result in a polymerization or curing whereby the (meth)acrylate-functionalized organic substance becomes part of a polymerized matrix or polymeric chain. In various embodiments of the invention, the (meth) acrylate-functionalized organic substance may contain one, two, three, four, five or more (meth)acrylate functional groups per molecule. Combinations of multiple (meth)acrylate-functionalized organic substances containing different numbers of (meth)acrylate groups may be utilized in the photocurable compositions of the present invention.

The photocurable compositions used in the present invention thus may contain one or more (meth)acrylate functionalized organic substances capable of undergoing free radical polymerization (curing) initiated by exposure to actinic radiation (e.g., ultraviolet light) or electron beam radiation. The (meth)acrylate-functionalized organic substances may be oligomers or monomers or, preferably, a combination of oligomer(s) and monomer(s).

Any of the following types of (meth)acrylate-functionalized organic substances may, for example, be employed in the photocurable compositions of the present invention, possibly or optionally in combination with one or more other types of polymerizing organic substances as co-reactants: monomers such as (meth)acrylate esters of aliphatic mono-alcohols, (meth)acrylate esters of alkoxylated aliphatic mono-alcohols, (meth)acrylate esters of aliphatic polyols, (meth)acrylate esters of alkoxylated aliphatic polyols, (meth)acrylate esters of aromatic ring-containing alcohols, and (meth)acrylate esters of alkoxylated aromatic ring-containing alcohols; and oligomers such as epoxy (meth) acrylates, polyether (meth)acrylates, urethane (meth)acrylates, polyester (meth)acrylates (including amine- and sulfide-modified derivatives thereof); and combinations thereof.

According to one aspect of the invention, the photocurable composition contains at least one hydroxyalkyl (meth) acrylate, such as hydroxyethyl methacrylate and/or hydroxypropyl methacrylate. For example, the photocurable composition may contain from 5 to 30 weight % in total of hydroxyalkyl (meth)acrylate, based on the total weight of polymerizing organic substances in the photocurable composition. However, in other embodiments, the photocurable composition may contain little or no hydroxyalkyl (meth) acrylate (e.g., less than 5 weight % or 0 weight %, based on the total weight of polymerizing organic substances), since at least some hydroxyalkyl (meth)acrylates have sensitizing properties.

According to another aspect of the invention, the photocurable composition contains at least one cycloalkyl (meth) acrylate, in particular isobornyl (meth)acrylate. For example, the photocurable composition may contain from 1 to 25 or 5 to 15 weight % of cycloalkyl (meth)acrylate (e.g., isobornyl methacrylate), based on the total weight of polymerizing organic substances in the photocurable composition. Cyclohexyl (meth)acrylates, tetrahydrofurfuryl (meth)acrylates, and cyclic trimethylolpropane formal (meth)acrylates represent other types of cycloalkyl (meth)acrylate useful in the present invention.

According to another aspect of the invention, the photocurable composition contains at least one ethylene glycol- or poly(ethylene glycol)-based (meth)acrylate, such as a poly (ethyleneglycol) di(meth)acrylate. Such substances may be described as (meth)acrylates of ethylene glycol and poly (ethylene glycol), wherein the polyethylene glycol may contain two or more oxyethylene units derived from ethylene oxide per molecule. In certain embodiments, the substance comprises an ethylene glycol segment or polyethylene glycol segment having a number average molecular weight of from about 100 g/mol to about 1000 g/mol. Such a segment may correspond to the structural formula $—(CH_2CH_2O)_n—$, wherein n is from 2 to 25 on average. For example, the photocurable composition may contain from 1 to 80 or 5 to 60 weight % of poly(ethylene glycol) di(meth) acrylate, based on the total weight of polymerizing organic substances in the photocurable composition.

Ethylene glycol di(meth)acrylate, diethylene glycol di(meth)acrylate, triethylene glycol di(meth)acrylate, PEG-9 di(meth)acrylate (containing an average of about 9 oxyethylene units per molecule), PEG200 di(meth)acrylate (containing a polyethylene glycol segment having a number average molecular weight of about 200 g/mol) and PEG600 di(meth)acrylate (containing a polyethylene glycol segment having a number average molecular weight of about 600 g/mol) represent other types of ethylene glycol- or poly (ethylene glycol)-based (meth)acrylates useful in the present invention. The use of such ethylene glycol- or poly(ethylene glycol)-based (meth)acrylates in the photocurable compositions is advantageous in that such substances generally are low- to non-sensitizing, unlike certain other types of (meth) acrylate-functionalized monomers.

In yet another aspect of the invention, the photocurable composition contains at least one (meth)acrylate-functionalized monomer containing three or more (meth)acrylate functional groups per molecule, in particular (meth)acrylates of polyols containing three or more hydroxyl groups per molecule and alkoxylated derivatives thereof such as glycerol, trimethylolpropane, ditrimethylolpropane, pentaerythritol, dipentaerythritol, triethylolpropane and ethoxylated and/or propoxylated derivatives thereof in which the polyol is reacted with 1 to 10 moles of ethylene oxide and/or propylene oxide per mole of polyol. For example, the photocurable composition may contain from 0.1 to 20 or 0.5 to 10 weight % in total of such (meth)acrylate-functionalized monomers containing three or more (meth)acrylate functional groups per molecule (e.g., trimethylolpropane trimethacrylate).

Suitable (meth)acrylate-functionalized oligomers include, for example, polyester (meth)acrylates, epoxy (meth)acrylates, polyether (meth)acrylates, urethane (meth)acrylates (sometimes also referred to as polyurethane (meth)acrylates or urethane (meth)acrylate oligomers) and combinations thereof, as well as amine-modified and sulfide-modified variations thereof. Certain of these (meth)acrylate-functionalized oligomers may function as flexibilizers in the cured articles obtained by curing of the photocurable composition, i.e., their inclusion helps to increase the flexibility of the cured articles prepared therefrom.

Exemplary polyester (meth)acrylates include the reaction products of acrylic or methacrylic acid or mixtures thereof with hydroxyl group-terminated polyester polyols. The reaction process may be conducted such that a significant concentration of residual hydroxyl groups remain in the polyester (meth)acrylate or may be conducted such that all or essentially all of the hydroxyl groups of the polyester polyol have been (meth)acrylated. The polyester polyols can be made by polycondensation reactions of polyhydroxyl functional components (in particular, diols) and polycarboxylic acid functional compounds (in particular, dicarboxylic acids and anhydrides). To prepare the polyester (meth) acrylates, the hydroxyl groups of the polyester polyols are then partially or fully esterified by reacting with (meth) acrylic acid, (meth)acryloyl chloride, (meth)acrylic anhydride or the like. Polyester (meth)acrylates may also be synthesized by reacting a hydroxyl-containing (meth)acrylate such as a hydroxyalkyl (meth)acrylate (e.g., hydroxyethyl acrylate) with a polycarboxylic acid. The polyhydroxyl functional and polycarboxylic acid functional components can each have linear, branched, cycloaliphatic or aromatic structures and can be used individually or as mixtures.

Examples of suitable epoxy (meth)acrylates include the reaction products of acrylic or methacrylic acid or mixtures thereof with glycidyl ethers or esters.

Exemplary polyether (meth)acrylate oligomers include, but are not limited to, the condensation reaction products of acrylic or methacrylic acid or mixtures thereof with polyetherols which are polyether polyols. Suitable polyetherols can be linear or branched substances containing ether bonds and terminal hydroxyl groups. Polyetherols can be prepared by ring opening polymerization of epoxides and other oxygen-containing heterocyclic compounds (e.g., ethylene oxide, 1,2-propylene oxide, butene oxide, tetrahydrofuran and combinations thereof) with a starter molecule. Suitable starter molecules include water, hydroxyl functional materials, polyester polyols and amines. Polyetherols may also be obtained by the condensation of diols such as glycols.

Urethane (meth)acrylates (sometimes also referred to as "polyurethane (meth)acrylates" or "urethane (meth)acrylate oligomers") capable of being used in the photocurable compositions of the present invention include urethanes based on aliphatic and/or aromatic polyester polyols, polyether polyols and polycarbonate polyols and aliphatic and/or aromatic polyester diisocyanates and polyether diisocyanates capped with (meth)acrylate end-groups.

In various embodiments, the urethane (meth)acrylates may be prepared by reacting aliphatic and/or aromatic polyisocyanates (e.g., diisocyanates, triisocyanates) with OH group terminated polyester polyols (including aromatic, aliphatic and mixed aliphatic/aromatic polyester polyols), polyether polyols, polycarbonate polyols, polycaprolactone polyols, polydimethysiloxane polyols, or polybutadiene polyols, or combinations thereof to form isocyanate-functionalized oligomers which are then reacted with hydroxyl-functionalized (meth)acrylates such as hydroxyethyl (meth) acrylate or hydroxypropyl (meth)acrylate to provide terminal (meth)acrylate groups. For example, the urethane (meth)acrylates may contain two, three, four or more (meth) acrylate functional groups per molecule. Other orders of addition may also be practiced to prepare the polyurethane (meth)acrylate, as is known in the art. For example, the hydroxyl-functionalized (meth)acrylate may be first reacted with a polyisocyanate to obtain an isocyanate-functionalized (meth)acrylate, which may then be reacted with an OH group terminated polyester polyol, polyether polyol, polycarbonate polyol, polycaprolactone polyol, polydimethysiloxane polyol, polybutadiene polyol, or a combination thereof. In yet another embodiment, a polyisocyanate may be first reacted with a polyol, including any of the aforementioned types of polyols, to obtain an isocyanate-functionalized polyol, which is thereafter reacted with a hydroxyl-functionalized (meth)acrylate to yield a polyurethane (meth)acrylate. Alternatively, all the components may be combined and reacted at the same time.

Any of the above-mentioned types of oligomers may be modified with amines or sulfides (e.g., thiols), following procedures known in the art. Such amine- and sulfide-modified oligomers may be prepared, for example, by reacting a relatively small portion (e.g., 2-15%) of the (meth) acrylate functional groups present in the base oligomer with an amine (e.g., a secondary amine) or a sulfide (e.g., a thiol), wherein the modifying compound adds to the carbon-carbon double bond of the (meth)acrylate in a Michael addition reaction.

Illustrative examples of suitable monomeric (meth)acrylate-functionalized organic substances include (meth)acrylated mono- and polyols (polyalcohols) and (meth)acrylated alkoxylated mono-alcohols and polyols. The mono-alcohols and polyols may be aliphatic (including one or more cycloaliphatic rings) or may contain one or more aromatic rings (as in the case of phenol or bisphenol A). "Alkoxylated" means that the base mono-alcohol or polyol has been reacted with one or more epoxides such as ethylene oxide and/or propylene oxide so as to introduce one or more ether moieties (e.g., $—CH_2CH_2—O—$) onto one or more hydroxyl groups of the mono-alcohol or polyol, prior to esterification to introduce one or more (meth)acrylate functional groups. For example, the amount of epoxide reacted with the mono-alcohol or polyol may be from about 1 to about 30 moles of epoxide per mole of mono-alcohol or polyol. Examples of suitable mono-alcohols include, but are not limited to, straight chain, branched and cyclic C1-C54 mono-alcohols (which may be primary, secondary or tertiary alcohols). For instance, the mono-alcohol may be a C1-C7 aliphatic mono-alcohol. In another embodiment, the mono-alcohol may be a C8-C24 aliphatic mono-alcohol (e.g., lauryl alcohol, stearyl alcohol). Examples of suitable polyols include organic compounds containing two, three, four or more hydroxyl groups per molecule such as glycols (diols), e.g., ethylene glycol, 1,2- or 1,3-propylene glycol, or 1,2-, 1,3- or 1,4-butylene glycol, neopentyl glycol, trimethylolpropane, triethylolpropane, pentaerythritol, glycerol and the like.

Representative, but not limiting, examples of suitable monomeric (meth)acrylate-functionalized compounds include: 1,3-butylene glycol di(meth)acrylate, 1,4-butanediol di(meth)acrylate, 1,6-hexanediol di(meth)acrylate, longer chain aliphatic di(meth)acrylates (such as those generally corresponding to the formula $H_2C{=}CRC({=}O)—O—(CH_2)_m—O—C({=}O)CR'{=}CH_2$, wherein R and R' are independently H or methyl and m is an integer of 8 to 24), alkoxylated (e.g., ethoxylated, propoxylated) hexanediol di(meth)acrylates, alkoxylated (e.g., ethoxylated, propoxylated) neopentyl glycol di(meth)acrylates, dodecyl di(meth) acrylates, cyclohexane dimethanol di(meth)acrylates, diethylene glycol di(meth)acrylates, dipropylene glycol di(meth) acrylates, alkoxylated (e.g., ethoxylated, propoxylated) bisphenol A di(meth)acrylates, ethylene glycol di(meth) acrylates, neopentyl glycol di(meth)acrylates, tricyclodecane dimethanol diacrylates, triethylene glycol di(meth)acrylates, tetraethylene glycol di(meth)acrylates, tripropylene glycol di(meth)acrylates, ditrimethylolpropane tetra(meth)acrylates, dipentaerythritol penta(meth)acrylates, alkoxylated (e.g., ethoxylated, propoxylated) pentaerythritol tetra(meth)acrylate, dipentaerythritol penta(meth)acrylates, pentaerythritol tetra(meth)acrylate, alkoxylated (e.g., ethoxylated, propoxylated) trimethylolpropane tri(meth) acrylates, alkoxylated (e.g., ethoxylated, propoxylated) glyceryl tri(meth)acrylates, trimethylolpropane tri(meth) acrylates, pentaerythritol tri(meth)acrylates, tris (2-hydroxy ethyl) isocyanurate tri(meth)acrylates, 2(2-ethoxyethoxy) ethyl (meth)acrylates, 2-phenoxyethyl (meth)acrylates, 3,3,5-trimethylcyclohexyl (meth)acrylates, alkoxylated lauryl (meth)acrylates, alkoxylated phenol (meth)acrylates, alkoxylated tetrahydrofurfuryl (meth)acrylates, caprolactone (meth)acrylates, cyclic trimethylolpropane formal (meth)acrylates, dicyclopentadienyl (meth)acrylates, diethylene glycol methyl ether (meth)acrylates, alkoxylated (e.g., ethoxylated, propoxylated) nonyl phenol (meth)acrylates, isobornyl (meth)acrylates, isodecyl (meth)acrylates, isooctyl (meth)acrylates, lauryl (meth)acrylates, methoxy polyethylene glycol (meth)acrylates, octyldecyl (meth)acrylates (also known as stearyl (meth)acrylates), tetrahydrofurfuryl (meth)acrylates, tridecyl (meth)acrylates, triethylene glycol ethyl ether (meth)acrylates, t-butyl cyclohexyl (meth)acrylates, dicyclopentadiene di(meth)acrylates, phenoxyethanol (meth)acrylates, octyl (meth)acrylates, decyl (meth)acrylates, dodecyl (meth)acrylates, tetradecyl (meth)acrylates, cetyl (meth)acrylates, hexadecyl (meth)acrylates, behenyl (meth)acrylates, diethylene glycol ethyl ether (meth)acrylates, diethylene glycol butyl ether (meth)acrylates, triethylene glycol methyl ether (meth)acrylates, dodecanediol di(meth)acrylates, dipentaerythritol penta/hexa(meth)acrylates, pentaerythritol tetra(meth)acrylates, alkoxylated (e.g., ethoxylated, propoxylated) pentaerythritol tetra(meth)acrylates, di-trimethylolpropane tetra(meth)acrylates, alkoxylated (e.g., ethoxylated, propoxylated) glyceryl tri(meth) acrylates, and tris (2-hydroxyethyl) isocyanurate tri(meth) acrylates, and combinations thereof.

Other types of polymerizing organic substances containing ethylenically unsaturated functional groups suitable for use in the photocurable compositions of the present invention include cyanoacrylates, vinyl esters, 1,1-diester-1-alkenes, 1,1-diketo-1-alkenes, 1-ester-1-keto-1-alkenes and itaconates, including methylene malonates and/or methylene beta-diketones.

The amount of (meth)acrylate-functionalized oligomer may be varied based on the viscosity of the oligomer or the tensile properties desired in the photocurable composition when cured. For example, the photocurable composition may contain from 1 to 80 or 5 to 60 weight % of (meth) acrylate-functionalized oligomer, based on the total weight of polymerizing organic substances in the photocurable composition. A suitable (meth)acrylate-functionalized oligomer could be di-[2-hydroxyethyl methacrylate] ("di-HEMA") trimethylhexyl dicarbamate (UDMA).

According to particularly preferred embodiments of the invention, the polymerizing organic substance(s) which make up components a) and b) of the photocurable composition is or are selected to be compatible with the core/shell copolymer(s) also present in the photocurable composition. As used herein, the term "compatible" means that a photocurable composition does not gel or increase in viscosity to an unacceptable degree when the components of the photocurable composition are combined (that is, the photocurable composition remains workable, i.e., capable of being applied and shaped in accordance with its intended end use application).

Photoinitiators

The photocurable compositions described herein include at least one photoinitiator and are curable with radiant energy (actinic radiation). A photoinitiator may be considered any type of substance that, upon exposure to radiation (e.g., actinic radiation), forms species that initiate the reaction and curing of polymerizing organic substances present in the photocurable composition, such as monomeric polymerizing organic substances as well as oligomeric polymerizing organic substances. Suitable photoinitiators include both free radical photoinitiators as well as cationic photoinitiators and combinations thereof. The photoinitiator should be selected so that it is susceptible to activation by photons of the wavelength associated with the actinic radiation intended to be used to cure the photocurable composition. Preferably, the photoinitiator or combination of photoinitiators should be active at the wavelength(s) of the ultraviolet light emitted by lamps commonly or conventionally found in nail salons.

Free radical polymerization initiators are substances that form free radicals when irradiated.

When the photocurable composition contains polymerizing organic substances containing polymerizable (reactive) ethylenically unsaturated functional groups such as (meth) acrylate functional groups, the use of free radical photoinitiators is especially preferred. Non-limiting types of free radical photoinitiators suitable for use in the photocurable compositions of the present invention include, for example, benzoins, benzoin ethers, acetophenones, benzyl, benzyl ketals, anthraquinones, phosphine oxides, α-hydroxyketones, phenylglyoxylates, α-aminoketones, benzophenones, thioxanthones, xanthones, acridine derivatives, phenazene derivatives, quinoxaline derivatives and triazine compounds. Examples of particular suitable free radical photoinitiators include, but are not limited to, 2-methylanthraquinone, 2-ethylanthraquinone, 2-chloroanthraquinone, 2-benzyanthraquinone, 2-t-butylanthraquinone, 1,2-benzo-9,10-anthraquinone, benzyl, benzoins, benzoin ethers, benzoin, benzoin methyl ether, benzoin ethyl ether, benzoin isopropyl ether, alpha-methylbenzoin, alpha-phenylbenzoin, Michler's ketone, acetophenones such as 2,2-dialkoxybenzophenones and 1-hydroxyphenyl ketones, benzophenone, 4,4'-bis-(diethylamino) benzophenone, acetophenone, 2,2-diethyloxyacetophenone, diethyloxyacetophenone, 2-isopropylthioxanthone, thioxanthone, diethyl thioxanthone, 1,5-acetonaphthylene, ethyl-p-dimethylaminobenzoate, benzil ketone, α-hydroxy keto, 2,4,6-trimethylbenzoyldiphenyl phosphine oxide, benzyl dimethyl ketal, 2,2-dimethoxy-1,2-diphenylethanone, 1-hydroxycylclohexyl phenyl ketone, 2-methyl-1-[4-(methylthio) phenyl]-2-morpholinopropanone-1, 2-hydroxy-2-methyl-1-phenyl-propanone, oligomeric α-hydroxy ketone, benzoyl phosphine oxides, phenylbis(2,4,6-trimethylbenzoyl)phosphine oxide, ethyl-4-dimethylamino benzoate, ethyl(2,4,6-trimethylbenzoyl) phenyl phosphinate, anisoin, anthraquinone, anthraquinone-2-sulfonic acid, sodium salt monohydrate, (benzene) tricarbonylchromium, benzil, benzoin isobutyl ether, benzophenone/1-hydroxycyclohexyl phenyl ketone, 50/50 blend, 3,3',4,4'-benzophenonetetracarboxylic dianhydride, 4-benzoylbiphenyl, 2-benzyl-2-(dimethylamino)-4'-morpholinobutyrophenone, 4,4'-bis(diethylamino)benzophenone, 4,4'-bis(dimethylamino)benzophenone, camphorquinone, 2-chlorothioxanthen-9-one, dibenzosuberenone, 4,4'-dihydroxybenzophenone, 2,2-dimethoxy-2-phenylacetophenone, 4-(dimethylamino)benzophenone, 4,4'-dimethylbenzil, 2,5-dimethylbenzophenone, 3,4-dimethylbenzophenone, diphenyl(2,4,6-trimethylbenzoyl)phosphine oxide/2-hydroxy-2-methylpropiophenone, 50/50 blend, 4'-ethoxyacetophenone, 2,4,6-trimethylbenzoyldiphenylphophine oxide, phenyl bis(2,4,6-trimethyl benzoyl) phosphine oxide, ferrocene, 3'-hydroxyacetophenone, 4'-hydroxyacetophenone, 3-hydroxybenzophenone, 4-hydroxybenzophenone, 1-hydroxycyclohexyl phenyl ketone, 2-hydroxy-2-methylpropiophenone, 2-methylbenzophenone, 3-methylbenzophenone, methybenzoylformate, 2-methyl-4'-(methylthio)-2-morpholinopropiophenone, phenanthrenequinone, 4'-phenoxyacetophenone, (cumene) cyclopentadienyl iron(ii) hexafluorophosphate, 9,10-diethoxy and 9,10-dibutoxyanthracene, 2-ethyl-9,10-dimethoxyanthracene, thioxanthen-9-one and combinations thereof.

Suitable cationic photoinitiators include any type of photoinitiator that, upon exposure to radiation such as actinic radiation, forms cations (e.g., Brönsted or Lewis acids) that initiate the reaction of the monomeric and (if present) oligomeric polymerizing organic substances in the photocurable composition. For example, a cationic photoinitiator may be comprised of a cationic portion and an anionic portion. The cationic portion of the photoinitiator molecule can be responsible for the absorption of UV radiation while the anionic portion of the molecule becomes a strong acid after UV absorption. Suitable cationic photoinitiators include, for example, onium salts with anions of weak nucleophilicity, such as halonium salts, iodonium salts (e.g., diaryliodonium salts such as bis(4-t-butylphenyl) iodonium perfluoro-1-butane sulfonate) or sulfonium salts (e.g., triarylsulfonium salts such as triarylsulfonium hexafluoroantimonate salts); sulfoxonium salts; and diazonium salts. Metallocene salts are another type of suitable cationic photoinitiator.

The amount of photoinitiator may be varied as may be appropriate depending upon the photoinitiator(s) selected, the amounts and types of polymerizing organic substances (monomeric and oligomeric) present in the photocurable composition, the radiation source and the radiation conditions used, among other factors. Typically, however, the amount of photoinitiator may be from 0.05% to 5%, preferably 0.1% to 2% by weight, based on the total weight of the photocurable composition.

Other Additives/Components

The photocurable compositions of the present invention may optionally contain one or more additives instead of or in addition to the above-mentioned ingredients. Such additives include, but are not limited to, antioxidants/photostabilizers, light blockers/absorbers, polymerization inhibitors, foam inhibitors, flow or leveling agents, colorants, pigments, dispersants (wetting agents, surfactants), slip additives, fillers, chain transfer agents, thixotropic agents, rheology modifiers, matting agents, impact modifiers (other than the core/shell copolymers and oligomeric polymerizing organic substances already mentioned), waxes or other various additives, including any of the additives conventionally utilized in the nail coating art.

To protect against premature gelling or curing of the photocurable composition, particularly in the presence of oxygen or other oxidant, one or more antioxidants may be included in the photocurable composition. Any of the antioxidants known in the art may be utilized, including for example phenol-based antioxidants, phosphorus-based antioxidants, quinone-type antioxidants and combinations thereof.

Examples of suitable phenol-based antioxidants may include hindered phenol-type antioxidants such as hexamethylene bis[(3,5-di-tert-butyl-4-hydroxyphenyl)propionic acid anide], 4,4'-thio bis(6-tert-butyl-m-cresol), 2,2'-methylene bis(4-methyl-5-tert-butylphenol), 2,2'-methylene bis (4-ethyl-6-tert-butylphenol), bis[3,3-bis(4-hydroxy-3-tert-butylphenyl)butyric acid]glycol ester, 2,2'-ethylidene bis(4,6-di-tert-butylphenol), 2,2'-ethylidene bis(4-sec-butyl-6-tert-butylphenol), 1,1,3-tris(2-methyl-4-hydroxy-5-tert-butylphenyl)butane, bis[2-tert-butyl-4-methyl-6-(2-hydroxy-3-tert-butyl-5-methylbenzyl)phenyl]terephthalate, 1,3,5-tris(3,5-di-tert-butyl-4-hydroxybenzyl)-2,4,6-trimethylbenzene, 1,3,5-tris[(3,5-di-tert-butyl-4-hydroxyphenyl) propionyloxyethyl]isocyanurate, tetrakis[methylene-3-(3,5-di-tert-butyl-4-hydroxyphenyl) propionate]methane, 2-tert-butyl-4-methyl-6-(2-acryloyloxy-3-tert-butyl-5-methylbenzyl)phenol, 3,9-bis[11-dimethyl-2-{(3-tert-butyl-4-hydroxy-5-methylphenyl)propionyloxy}ethyl]-2,4,8,10-tetraoxaspiro[5.5]undecane, triethylene glycol bis[(3-tert-butyl-4-hydroxy-5-methylphenyl)propionate], and n-octadecyl-3-4'-hydroxy-3',5'-di-tert-butylphenyl)butane. Butylated hydroxy toluene (BHT) is an example of a preferred antioxidant.

Examples of suitable phosphorus-based antioxidants may include phosphites, phosphonites and the like such as trisnonylphenyl phosphite, tris(2,4-di-tert-butylphenyl)phosphite, tris[2-tert-butyl-4-(3-tert-butyl-4-hydroxy-5-methylphenylthio)-5-methylphenyl]phosphite, tridecyl phosphite, octyldiphenyl phosphite, di(decyl)monophenyl phosphite, di(tridecyl)pentaerythritol diphosphite, distearyl pentaerythritol diphosphite, di(nonylphenyl)pentaerythritol diphosphite, bis(2,4-di-tert-butylphenyl)pentaerythritol diphosphite, bis(2,6-di-tert-butyl-4-methylphenyl)pentaerythritol diphosphite, bis(2,4,6-tri-tert-butylphenyl)pentaerythritol diphosphite, tetra(tridecyl)isopropylidene diphenol diphosphite, tetra(tridecyl)-4,4'-n-butylidene bis(2-tert-butyl-5-methylphenol)diphosphite, hexa(tridecyl)-1,1,3-tris (2-methyl-4-hydroxy-5-tert-butylphenyl)butane triphosphite, tetrakis(2,4-di-tert-butylphenyl)biphenylene diphosphonite, 9,10-dihydro-9-oxa-10-phosphaphenanthrene-10-oxide, 2,2-methylene bis(4-methyl-6-tert-butylphenyl)-2-ethylhexyl phosphite, and 4-[3-[(2,4,8,10-tetra-tert-butyldibenzo[d,f][1,3,2]dioxaphosphepin)-6-yloxy]propyl]-2-methyl-6-tert-butylphenol.

Quinone-type antioxidants, such as the mono methyl ether of hydroquinone (MEHQ), may also be used. Phenothiazine (RTZ) and vitamin E are examples of other suitable antioxidants useful in the present invention.

Typically, one or more antioxidants may be included in the photocurable composition in a total amount of up to 4% by weight, e.g., 0.05 to 2% by weight, based on the weight of the photocurable composition.

Advantageously, the photocurable compositions utilized in the present invention may be formulated to be solvent-free, i.e., free of any non-reactive volatile substances (substances having a boiling point at atmospheric pressure of 150° C. or less). For example, the photocurable compositions may contain little or no non-reactive solvent, e.g., less than 10% or less than 5% or less than 1% or even 0% non-reactive solvent, based on the total weight of the photocurable composition. In the context of the present invention, "non-reactive" refers to a substance that does not react when exposed to actinic radiation, i.e., a non-polymerizing substance. Such solvent-less or low-solvent compositions may be formulated using various components, including for example low viscosity reactive diluents (such as monomeric polymerizing organic substances), which are selected so as to render the photocurable composition sufficiently low in viscosity, even without solvent being present, that the photocurable composition can be easily applied at a suitable application temperature to a substrate surface such as the surface of a nail of a subject.

However, in other embodiments, the photocurable composition which is used does contain some amount of non-reactive solvent, in particular some amount of volatile non-reactive solvent (having a boiling point at atmospheric pressure of not more than 150° C.). As an example, if the photocurable composition is to be formulated for use as a relatively low viscosity top coat, base coat, color coat or nail polish, one or more non-reactive solvents may be included. For example, the photocurable composition may be comprised of at least 0.5, at least 1, at least 5, or at least 10% by weight non-reactive solvent based on the total weight of the photocurable composition. The photocurable composition could comprise not more than 50, not more than 25, or not more than 15% by weight non-reactive solvent based on the total weight of the photocurable composition. The amount of non-reactive solvent may be adjusted to achieve a target viscosity value, as the non-reactive solvent will generally reduce the viscosity of a photocurable composition. Two or more non-reactive solvents may be used in combination. Suitable non-reactive solvents include esters (such as ethyl acetate and butyl acetate), ethers, ketones, glycol ethers, alcohols, hydrocarbons and combinations thereof.

In certain embodiments of the invention, the photocurable composition is a liquid at 25° C. For example, the photocurable composition may be a flowable and/or self-levelling liquid at 25° C. In other embodiments, however, the photocurable composition may be a gel at 25° C. Such a gel may be non-flowable.

The viscosity of the photocurable composition at 25° C. may be varied widely, depending upon the intended end use application as discussed in more detail below. For example, the viscosity of the photocurable composition at 25° C. may range from 100 cps to 5,000,000 cps.

In various embodiments of the invention (for example, where the photocurable composition is intended for use as a UV gel polish, base coat, color coat or top coat), the photocurable compositions described herein are formulated to have a relatively low viscosity at ambient or room temperature. For example, the viscosity of the photocurable composition may be selected or adjusted, by varying the components present and their relative ratios, to provide a viscosity at 25° C. which is not more than 100,000 cps, not more than 50,000 cps, not more than 25,000 cps, or not more than 10,000 cps as measured by a Brookfield DV3T Cone and Plate Rheometer with measurements conducted at 25° C. on 0.5 mL samples using a CPE-52Z cone. The viscosity at 25° C. could, for example, be at least 100 cps or at least 500 cps.

However, in other embodiments of the invention, the photocurable compositions described herein are formulated to have a relatively high viscosity at ambient or room temperature. Such high viscosity photocurable compositions may be of interest where it is intended to be applied to a nail surface and then sculpted (i.e., a builder gel, sculpting gel, or nail extension). For example, the viscosity of the photocurable composition may be selected or adjusted, by varying the components present and their relative ratios, to provide a viscosity at 25° C. which is at least 200,000 cps, at least 300,000 cps, or at least 400,000 cps, as measured by a Brookfield DV3T Cone and Plate Rheometer with measurements conducted at 25° C. on 0.5 mL samples using a CPE-52Z cone. At the same time, the viscosity should not be so high that the photocurable composition becomes difficult to apply and/or shape on a nail surface. The viscosity at 25° C. could, for example, be not greater than 5,000,000 cps or not greater than 4,000,000 cps.

The viscosity and other rheological properties of the photocurable composition may be selected such that when a portion of the photocurable composition is applied onto a nail surface, it does not move easily until it is pushed into a desired shape (sculpted) by a manicurist tool, such as a brush, pusher and/or spatula. The pushing and sculpting of the photocurable composition into a desired shape may be done neat, or it may be done with the aid of a low viscosity liquid (such as a non-reactive solvent and/or a reactive diluent, such as a (meth)acrylate-functionalized monomer) which lowers, at least locally, the viscosity of the photocurable composition. According to advantageous embodiments of the invention, when the photocurable composition is either in neat form or is admixed with such a liquid (in limited amounts), the photocurable composition remains firm (but shapable) and does not run. An operator, such as a nail technician, may optionally control the viscosity through the application of such a suitable liquid, which may be done only in selected areas of the portion of photocurable composition on the nail surface, until the photocurable composition is cured by exposure to actinic radiation (e.g., UV light).

Although in one embodiment only a single portion of a photocurable composition is applied to an individual nail prior to a photocuring step, it is also possible in other embodiments of the invention for a plurality of photocurable composition portions to be applied. For example, a portion of a first photocurable composition may be applied and shaped followed by a portion of a second photocurable composition (which may be pigmented or colored differently from the first photocurable composition or which may differ compositionally in other ways) with the second photocurable composition portion being shaped prior to both portions being photocured to provide the cured nail coating.

Formulation of the Photocurable Composition

The relative weight proportions of component (a) (the at least one (meth)acrylate-functionalized monomer), component (b) (the at least one (meth)acrylate-functionalized oligomer), component (c) (the particles of at least one core/shell copolymer) and component (d) (the at least one photoinitiator) are not believed to be particularly critical and may be varied as desired based on the particular components selected and the characteristics sought in the photocurable composition and cured articles obtained therefrom. For example, the photocurable composition in certain embodiments may comprise 5 to 45 wt % component (a), 5 to 60 wt % component (b), 10 to 60 wt % component (c), and 0.1 to 10 wt % component (d), wherein the weight of (a), (b), (c) and (d) equals 100% in total (meaning that the aforementioned wt % ranges for each of (a), (b), (c) and (d) is based on the combined weights of those components, not the total weight of the photocurable composition which may contain components in addition to (a), (b), (c) and (d)).

According to preferred embodiments, the components of the photocurable composition are selected so that the photocurable composition is liquid at least in the temperature range between 0° C. and 60° C. As used in this context, the term "liquid" does not preclude the possibility that some portion of the photocurable composition (in particular, the core/shell copolymer) may be present in the form of small, well-dispersed particles in an otherwise liquid matrix.

Generally speaking, photocurable compositions in accordance with the invention may be prepared by combining the individual components. If a (meth)acrylic polymer is a component of the photocurable composition, the core/shell copolymer and (meth)acrylic polymer may be supplied separately to the photocurable composition or together as parts of a polymer composition obtained, for example, through a core/shell copolymerization process in which the (meth)acrylic polymer is prepared as one of the stages. The photocurable composition may also be produced using a master batch approach, wherein a master batch comprised of core/shell copolymer, (meth)acrylic polymer and a relatively small amount of polymerizing organic substance is first prepared which is later combined with additional polymerizing organic substance(s) and possibly other components (such as photoinitiator) to yield the final photocurable composition to be employed in the manufacture of a cured nail coating.

Use of the Photocurable Composition in Forming Nail Coatings

The photocurable compositions utilized in the present invention are photocured (i.e., cured by exposure to actinic radiation such as light, in particular visible or UV light). However, such photocuring is not conducted until after the photocurable composition is applied to a nail surface and, in certain embodiments, shaped into a desired configuration. For example, a method of forming a cosmetic nail coating comprises the steps of placing the above-described photocurable composition onto a nail of a subject, optionally shaping the photocurable composition, and exposing the photocurable composition to UV light.

The placement of a portion (such as a bead) of the photocurable composition may be directly performed by the operator (which may be a technician or the individual whose nails are being coated) directly by squeezing it from a tube container or pushing it from a syringe with a plunger on to the nail or an application tool. Alternatively, the application of the photocurable composition may be completed with the help of an application tool such as an acrylic or gel brush, pusher and/or a spatula or other such tool conventionally used for applying nail coating products.

After the placement of the bead of the photopolymerizable composition onto the nail, the operator may work the photocurable composition to move it into a desired location and form it into a desired shape with or without the use of a nail form. A nail mold could also be used, wherein a portion of the photocurable composition (preferably in the form of a high viscosity liquid or gel) is applied to a surface of the nail mold, the applied portion of photocurable composition is shaped within the nail mold, the nail mold containing the shaped portion of photocurable composition is applied to a nail of a subject (the surface having the shaped portion of the photocurable composition being brought into contact with the surface of the nail), the photocurable composition being cured by exposure to actinic radiation to provide a cured nail coating, and the nail mold then separated from the cured nail coating.

After the photocurable composition is applied to a nail surface and optionally shaped or formed, the nail having the photocurable composition disposed thereon is exposed to actinic radiation, such as UV light, under conditions effective to cure the photocurable composition. A suitable source of UV light may be a UV lamp, such as the UV lamps commonly used in nail salons. Such a UV lamp may operate at any wavelength required to cure the photocurable composition, such as between 320 run and 420 nm. The exposure time should be as long enough to achieve curing of the photocurable composition. This may be 5 seconds to 6 minutes, for example.

The term “UV lamp” is meant to be interpreted broadly. It refers to any source of electromagnetic radiation that exhibits light in the 320 nm to 420 nm range at sufficient enough strength to cure the photocurable composition used in the present invention. The term “UV lamp” includes traditional UV lamps that contain fluorescent lamps, such as compact fluorescent light bulbs, that give off UV light in the above-described ranges. The term “UV lamp” also refers to newer sources of light or UV radiation, such as light-emitting diode lamps (commonly referred to as “LED lamps”) that emit electromagnetic radiation which includes UV light in the 320 nm to 420 nm range at sufficient enough strength to cure the photocurable composition. The term “UV lamp” also refers to any other type of source of light that comprises UV light in the 320 nm to 420 nm range at sufficient enough strength to cure the photocurable composition.

Following a curing step, the cured nail coating may be subjected to one or more further procedures such as trimming, sanding, buffing, polishing, decorating or the like. It is also possible to form multiple layers of photocured coatings on a nail surface, wherein a first layer of the photocurable composition is applied to a nail surface, optionally shaped and cured and at least one further layer of the photocurable composition thereafter applied on top of the first cured layer, optionally shaped and then also cured.

Packaged Articles Containing Photocurable Composition

The above-described photocurable compositions may be packaged in a suitable container and stored and/or transported prior to use in forming the photocurable composition into a cured nail coating. The packaged article may thus comprise a container and a photocurable composition disposed within the container, wherein the packaged article has a dispensing component capable of dispensing the photocurable composition from the container. Suitable types of containers include tubes, bottles (including jars or pots), and syringes (equipped with plungers). The container may be rigid or flexible; for example, the container may be a flexible tube or bottle which allows a user to squeeze the container to facilitate dispensing of the photocurable composition through an aperture in the container. The container may be fitted with a releasable closure such as a screw or press-on cap or flap that permits the contents of the container to be sealed for protection or against accidental discharge when not in use. Such a releasable closure may include an application tool such as a brush. It will generally be preferred for the container to be opaque, to enhance the storage stability of the photocurable composition contained therein. The dispensing component could, for example, be a brush, foam applicator, wick, nozzle, roller, needle or aperture (orifice) or the like. As an example, the dispensing component could be an aperture that is configured to deliver a desired portion, such as a bead, of the photocurable composition, either directly onto a nail surface or onto an applicator (application device) such as a brush, pusher or spatula which is then used to transfer the portion of photocurable composition onto the nail surface.

Also contemplated by the present invention are kits comprised of a packaged article comprising a container and a photocurable composition disposed within the container, at least one application device, and instructions for dispensing, applying and curing the photocurable composition to provide a nail coating. The packaged article may have a dispensing component as previously described. The instructions may be provided in the form of an instruction sheet and/or printed on a package which contains the components of the kit.

ASPECTS OF THE INVENTION

Certain illustrative, non-limiting aspects of the invention may be summarized as follows:

Aspect 1: A coating on a nail, wherein the coating is the photocured product of a photocurable composition, wherein the photocurable composition comprises:

a). at least one (meth)acrylate-functionalized monomer;

b). at least one (meth)acrylate-functionalized oligomer;

c). particles of at least one core/shell copolymer; and d). at least one photoinitiator.

Aspect 2: The coating of Aspect 1, wherein the core/shell copolymer is comprised of a core comprising an elastomeric polymer having a glass transition temperature less than 0° C. and at least one shell comprising a non-elastomeric polymer having a glass transition temperature of at least 30° C.

Aspect 3: The coating of Aspect 1 or 2, wherein the particles of the at least one core/shell copolymer are suspended in a liquid matrix comprised of a) and b).

Aspect 4: The coating of any one of Aspects 1 to 3, wherein the particles of the at least one core/shell copolymer have an average particle size of from 25 to 900 nm.

Aspect 5: The coating of any one of Aspects 1 to 4, wherein the photocurable composition is comprised of from 0 to 20% by weight in total, based on the weight of the photocurable composition, of at least one non-reactive solvent.

Aspect 6: The coating of any one of Aspects 1 to 5, wherein the photocurable composition is comprised of from 1 to 60%, 5 to 55%, or 10 to 50% by weight of the particles of the at least one core/shell copolymer based on the total weight of the photocurable composition.

Aspect 7: The coating of any one of Aspects 1 to 6, wherein the at least one shell comprises, in polymerized form, at least one monomer selected from the group consisting of alkyl methacrylates having a C1-C12 alkyl chain, C6-C12 vinyl aromatic organic compounds, acrylonitrile and combinations thereof, wherein the shell is optionally crosslinked.

Aspect 8: The coating of any one of Aspects 1 to 7, wherein the at least one shell comprises, in polymerized form, methyl methacrylate, wherein the shell is optionally crosslinked.

Aspect 9: The coating of any one of Aspects 1 to 8, wherein the core comprises, in polymerized form, at least one monomer selected from the group consisting of C4-C12 conjugated dienes and C1-C12 alkyl acrylates.

Aspect 10: The coating of any one of Aspects 1 to 9, wherein the core/shell copolymer is selected from the group consisting of:

a). core/shell copolymers comprising a core comprised of butyl acrylate in polymerized form and a shell comprised of methyl methacrylate in polymerized form; and b). core/shell copolymers comprising a core comprised of styrene and butadiene in copolymerized form and a shell comprised of methyl methacrylate in polymerized form.

Aspect 11: The coating of any one of Aspects 1 to 10, wherein the core is from 60% to 95% by mass of the total mass of the core/shell copolymer.

Aspect 12: The coating of any one of Aspects 1 to 11, wherein the at least one (meth)acrylate-functionalized monomer includes at least one monomer selected from the group consisting of hydroxyethyl methacrylate, hydroxypropyl methacrylate, isobornyl methacrylate, polyethylene glycol dimethacrylates and trimethylolpropane trimethacrylate.

Aspect 13: The coating of any one of Aspects 1 to 12, wherein the at least one (meth)acrylate-functionalized oligomer includes at least one (meth)acrylate-functionalized urethane oligomer.

Aspect 14: The coating of any one of Aspects 1 to 13, wherein the at least one or more photoinitiators are present in a total amount of from 0.1-5% based on the total weight of the photocurable composition.

Aspect 15: The coating of any one of Aspects 1 to 14, wherein the photocurable composition has a viscosity of from 100 to 5,000,000 cps at 25° C.

Aspect 16: The coating of any one of Aspects 1 to 15, wherein the photocurable composition is additionally comprised of at least one (meth)acrylic polymer which is not a core/shell copolymer.

Aspect 17: The coating of any one of Aspects 1 to 16, wherein the coating has an impact strength, as measured by energy loss per area, of at least 15 J/m or at least 20 J/m at 25° C.

Aspect 18: The coating of any one of Aspects 1 to 17, wherein the nail is a human fingernail or toenail.

Aspect 19: A method of forming a coating on a nail, comprising the steps of:

a) placing a photocurable composition onto a surface of a nail; and b) exposing the photocurable composition to ultraviolet or visible light;

wherein the photocurable composition comprises at least one (meth)acrylate-functionalized monomer; at least one (meth)acrylate-functionalized oligomer; particles of at least one core/shell copolymer; and at least one photoinitiator or is in accordance with the photocurable composition of any one of Aspects 1 to 18.

Aspect 20: The method of Aspect 19, wherein the photocurable composition is placed onto the surface of the nail and formed into a continuous layer before being photocured.

Aspect 21: A packaged article comprising a container and a photocurable composition disposed within the container, wherein the packaged article has a dispensing component capable of dispensing the photocurable composition from the container and the photocurable composition comprises at least one (meth)acrylate-functionalized monomer; at least one (meth)acrylate-functionalized oligomer; particles of at least one core/shell copolymer; and at least one photoinitiator or is in accordance with the photocurable composition of any one of Aspects 1 to 18.

Aspect 22: The packaged article of Aspect 21, wherein the container is a tube, bottle or syringe.

Aspect 23: The packaged article of Aspect 21 or 22, wherein the dispensing component is a brush, foam applicator, wick, nozzle, roller, needle or aperture.

Aspect 24: A kit, comprising a packaged article comprising a container and a photocurable composition disposed within the container, at least one application device, and instructions for dispensing, applying and curing the photocurable composition to provide a nail coating, wherein the photocurable composition comprises at least one (meth) acrylate-functionalized monomer; at least one (meth)acrylate-functionalized oligomer; particles of at least one core/shell copolymer; and at least one photoinitiator or is in accordance with the photocurable composition of any one of Aspects 1 to 18.

Aspect 25: The kit of Aspect 24, wherein the at least one application device includes at least one of a brush, pusher or spatula.

Within this specification, embodiments have been described in a way which enables a clear and concise specification to be written, but it is intended and will be appreciated that embodiments may be variously combined or separated without departing from the invention.

For example, it will be appreciated that all preferred features described herein are applicable to all aspects of the invention described herein.

In some embodiments, the invention herein can be construed as excluding any element or process step that does not materially affect the basic and novel characteristics of the invention. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

EXAMPLES

Two base photocurable compositions (Base Formulations 1 and 2) were prepared using the components listed in Table 1. The amounts listed are in parts by weight. All the components (except the urethane oligomer) were added to a 4 oz amber glass jar, then mixed at 60° C. on a roller for 30 minutes. The urethane oligomer was then added to the jar and the formulation further mixed at 60° C. on the roller for an additional 1.5 hours to give a clear, viscous solution.

TABLE 1

| Component | Base Formulation 1 | Base Formulation 2 |
|---|---|---|
| CN9893 difunctional urethane oligomer (Sartomer) | 69.2 | — |
| CN1964 urethane dimethacrylate oligomer (Sartomer) | — | 69.2 |
| SR423A isobornyl methacrylate (Sartomer) | 9.1 | 9.1 |
| SR350 trimethylolpropane trimethacrylate (Sartomer) | 1.7 | 1.7 |
| Hydroxyethyl methacrylate | 6.2 | 6.2 |
| Hydroxypropyl methacrylate | 11.2 | 11.2 |
| phosphine oxide photoinitiator | 1.5 | 1.5 |
| ketone photonitiator | 1.1 | 1.1 |

Six different polymeric powders were blended into each of Base Formulation 1 and 2 at varying percentages (10-40% by weight, based on the total weight of the Base Formulation+polymeric powder).

The polymeric powders used were as described in Table 2. Plastistrength®, Durastrength® and Clearstrength® are all registered trademarks of Arkema.

TABLE 2

| Polymeric Powder | Type of Polymer |
|---|---|
| Plastistrength ® 580 | High molecular weight acrylic copolymer (not core/shell) |
| Polymer A | High molecular weight acrylic copolymer (not core/shell) |
| Durastrength ® 200 | Polybutylacrylate core, polymethyl methacrylate shell |
| Durastrength ® 350 | Polybutylacrylate core, polymethyl methacrylate shell |
| Durastrength ® 440 | Acrylate-based core/shell copolymer |
| Clearstrength ® XT-100 | Polybutadiene-co-styrene core, polymethylmethacrylate shell |

Curable compositions were prepared from the Base Formulations and the polymeric powders in accordance with the following procedure. To a Flacktek® high speed mixer cup was added 20 g of either Base Formulation 1 or Base Formulation 2. Five grams of a specified polymeric powder were added and the mixture high speed mixed at 3000 RPM for 4 minutes. In certain cases a slightly hazy low viscosity liquid and in other cases a slightly hazy high viscosity gel was obtained. The difference in the consistency depends on amount of monomer and amount of oligomer and/or amount and type of core/shell particle.

A Brookfield DV3T Cone and Plate Rheometer was used to measure the viscosity of each of the resulting photocurable compositions. All measurements were conducted at 25° C. on 0.5 mL samples using a CPE-52Z cone. Shear rate was measured and data were collected and analyzed using Rheocalc software. The viscosities measured are reported in Table 3. By way of comparison, a commercial acrylic nail builder/sculpting gel product was found to have a viscosity of 2,500,000 cps.

TABLE 3

| Curable Composition | Viscosity (cps) |
|---|---|
| 20% by weight Plastistrength ® 580 in 80% by weight Base Formulation 1 | 625,800 |
| 20% by weight Polymer A in 80% by weight Base Formulation 1 | 225,000 |
| 20% by weight Durastrength ® 350 in 80% by weight Base Formulation 2 | 385,800 |
| 20% by weight Durastrength ® 440 in 80% by weight Base Formulation 2 | 9,900 |
| 20% by weight Durastrength ® 440 in 80% by weight Base Formulation 1 | 200,000 |
| 20% by weight Clearstrength ® XT-100 in 80% by weight Base Formulation 2 | 6,830 |
| 20% by weight Clearstrength ® XT-100 in 80% by weight Base Formulation 1 | 568,000 |

Impact testing on the photocurable compositions was performed in accordance with the following procedure. Three samples of each photocurable composition were warmed in an oven at 60° C., applied into silicone molds, and cured using a Phoseon LED curing lamp at 395 nm and 30 fpm. The resultant cured bricks were notched and their impact strength measured after being allowed to equilibrate overnight at 50% RH. A Zwick/Roell HIT5.5P Izod impact tester was used to measure the impact strength of the bricks. The results obtained are shown in Table 4. If a high molecular weight polymeric powder containing an acrylic copolymer (Polymer A) is used, the impact strength is very low (8.8 J/m). However, photocurable compositions containing a core/shell acrylic impact modifier (Durastrength® 440) that has a rubbery core exhibit a two to three-fold increase in the impact strength of the cured material (19.6 and 28.7 J/m depending on the base formulation). The difference between Durastrength® 350 and Durastrength® 440 is the size of the rubbery core. The impact strength achieved using Durastrength® 440 is higher than what is observed using Durastrength® 350. Photocurable compositions containing Clearstrength® XT-100 in both base formulations have, when cured, impact strengths of 29.8 J/m and 39.3 J/m, respectively. By way of comparison, a commercial acrylic nail builder/sculpting gel product was found to have an average energy loss per area of 12.7 J/m when cured and tested in the same way.

TABLE 4

| Curable Composition | Energy Loss per Area (J/m) | Ave. Energy Loss per area (J/m) |
|---|---|---|
| Commercial Sculpting Gel Product (Comparative) | 13.54, 13.78, 10.76 | 12.7 |
| 20% by weight Polymer A in 80% by weight Base Formulation 1 (Comparative) | 10.5, 7.42, 8.33 | 8.8 |
| 20% by weight Durastrength ® 350 in 80% by weight Base Formulation 2 (Invention) | 10.85, 11.77, 7.48 | 10.0 |
| 20% by weight Durastrength ® 440 in 80% by weight Base Formulation 2 (Inventive) | 21.44, 18.43, 18.95 | 19.6 |
| 20% by weight Durastrength ® 440 in 80% by weight Base Formulation 1 (Invention) | 15.42, 42.39, 28.54 | 28.7 |
| 20% by weight Clearstrength ® XT-100 in 80% by weight Base Formulation 2 (Inventive) | 24.54, 21.58, 32.71, 40.32 | 29.8 |
| 20% by weight Clearstrength ® XT-100 in 80% by weight Base Formulation 1 (Inventive) | 46.85, 38.77, 31.76, 39.74 | 39.3 |

The invention claimed is:

1. A coating on a nail, wherein the coating is the photocured product of a photocurable composition, wherein the photocurable composition comprises:

a). at least one (meth)acrylate-functionalized monomer;

b). at least one (meth)acrylate-functionalized oligomer;

c). particles of at least one core/shell copolymer comprising a core comprised of styrene and butadiene in copolymerized form and a shell comprised of methyl methacrylate in polymerized form; and d). at least one photoinitiator.

2. The coating of claim 1, wherein the core/shell copolymer is comprised of a core comprising an elastomeric polymer having a glass transition temperature less than 0° C. and at least one shell comprising a non-elastomeric polymer having a glass transition temperature of at least 30° C.

3. The coating of claim 1, wherein the particles of the at least one core/shell copolymer are suspended in a liquid matrix comprised of a) and b).

4. The coating of claim 1, wherein the photocurable composition is comprised of from 0 to 20% by weight in total, based on the weight of the photocurable composition, of at least one non-reactive solvent.

5. The coating of claim 1, wherein the photocurable composition is comprised of from 1 to 60% by weight of the particles of the at least one core/shell copolymer based on the total weight of the photocurable composition.

6. The coating of claim 1, wherein the core is from 60% to 95% by mass of the total mass of the core/shell copolymer.

7. The coating of claim 1, wherein the at least one (meth)acrylate-functionalized monomer includes at least one monomer selected from the group consisting of hydroxyethyl methacrylate, hydroxypropyl methacrylate, isobornyl methacrylate, polyethylene glycol dimethacrylates and trimethylolpropane trimethacrylate.

8. The coating of claim 1, wherein the at least one (meth)acrylate-functionalized oligomer includes at least one (meth)acrylate-functionalized urethane oligomer.

9. The coating of claim 1, wherein the at least one or more photoinitiators are present in a total amount of from 0.1 to 5% based on the total weight of the photocurable composition.

10. The coating of claim 1, wherein the photocurable composition has a viscosity of from 100 to 5,000,000 cps at 25° C.

11. The coating of claim 1, wherein the photocurable composition is additionally comprised of at least one (meth) acrylic polymer which is not a core/shell copolymer.

12. The coating of 1, wherein the coating has an impact strength, as measured by energy loss per area, of at least 15 J/m at 25° C.

13. The coating of claim 1, wherein the nail is a human fingernail or toenail.

14. A method of forming a coating on a nail, comprising the steps of:

a) placing a photocurable composition onto a surface of a nail; and b) exposing the photocurable composition to ultraviolet or visible light;

wherein the photocurable composition comprises at least one (meth)acrylate-functionalized monomer; at least one (meth)acrylate-functionalized oligomer; particles of at least one core/shell copolymer comprising a core comprised of styrene and butadiene in copolymerized form and a shell comprised of methyl methacrylate in polymerized form; and at least one photoinitiator.

15. The method of claim 14, wherein the photocurable composition is placed onto the surface of the nail and formed into a continuous layer before being photocured.

16. A packaged article comprising a container and a photocurable composition disposed within the container, wherein the packaged article has a dispensing component for dispensing the photocurable composition from the container and the photocurable composition comprises at least one (meth)acrylate-functionalized monomer; at least one (meth) acrylate-functionalized oligomer; particles of at least one core/shell copolymer comprising a core comprised of styrene and butadiene in copolymerized form and a shell comprised of methyl methacrylate in polymerized form; and at least one photoinitiator.

17. The packaged article of claim 16, wherein the container is a tube, a bottle or a syringe.

18. The packaged article of claim 16, wherein the dispensing component is a brush, a foam applicator, a wick, a nozzle, a roller, a needle or an aperture.

19. A kit, comprising a packaged article comprising a container and a photocurable composition disposed within the container, at least one application device, and instructions for dispensing, applying and curing the photocurable composition to provide a nail coating, wherein the photocurable composition comprises at least one (meth)acrylate-functionalized monomer; at least one (meth)acrylate-functionalized oligomer; particles of at least one core/shell copolymer comprising a core comprised of styrene and butadiene in copolymerized form and a shell comprised of methyl methacrylate in polymerized form; and at least one photoinitiator.

20. The kit of claim 19, wherein the at least one application device includes at least one of a brush, a pusher or a spatula.

21. The coating of claim 1, wherein the core is comprised of styrene, butadiene, and at least one additional co-monomer in copolymerized form.

22. The coating of claim 1, wherein the shell is comprised of methyl methacrylate and at least one co-monomer in copolymerized form.

* * * * *